US012661069B2

(12) United States Patent
Sinha

(10) Patent No.: US 12,661,069 B2
(45) Date of Patent: Jun. 23, 2026

(54) SYSTEM AND METHOD FOR VALIDATING CARDIOVASCULAR PARAMETER MONITORS

(71) Applicant: Midmark Corporation, Versailles, OH (US)

(72) Inventor: Tuhin Sinha, Burlingame, CA (US)

(73) Assignee: Midmark Corporation, Versailles, OH (US)

( * ) Notice: Subject to any disclaimer, the term of this patent is extended or adjusted under 35 U.S.C. 154(b) by 392 days.

(21) Appl. No.: 18/224,174

(22) Filed: Jul. 20, 2023

(65) Prior Publication Data

US 2023/0355182 A1    Nov. 9, 2023

Related U.S. Application Data

(62) Division of application No. 17/688,514, filed on Mar. 7, 2022, now Pat. No. 11,744,523.

(Continued)

(51) Int. Cl.
*A61B 5/00* (2006.01)
*A61B 5/022* (2006.01)
*A61B 5/0295* (2006.01)

(52) U.S. Cl.
CPC ........ *A61B 5/7221* (2013.01); *A61B 5/02208* (2013.01); *A61B 5/02233* (2013.01); *A61B 5/0295* (2013.01)

(58) Field of Classification Search
CPC .............. A61B 5/7221; A61B 5/02208; A61B 5/02233; A61B 5/0295; A61B 5/021;

(Continued)

(56) References Cited

U.S. PATENT DOCUMENTS 5,649,543 A    7/1997   Hosaka et al.
6,337,629 B1   1/2002   Bader
(Continued)

FOREIGN PATENT DOCUMENTS

CN        103826532 A      5/2014
CN        104337509 A      2/2015
(Continued)

OTHER PUBLICATIONS

International Search Report and Written Opinion for application No. PCT/US20/053785 dated Jan. 21, 2021.

(Continued)

*Primary Examiner* — Navin Natnithithadha
(74) *Attorney, Agent, or Firm* — FBT Gibbons LLP

(57) ABSTRACT

A system or method for validating an unvalidated cardiovascular parameter monitor can include receiving a plurality of reference cardiovascular parameter datasets, each reference cardiovascular parameter dataset associated with a patient of a plurality of patients; receiving a plurality of test cardiovascular parameter measurements, each test cardiovascular parameter measurement includes a cardiovascular parameter measured for a patient of the plurality of patients; and validating the cardiovascular parameter monitor based on an analysis of the plurality of reference cardiovascular measurements and the plurality of test cardiovascular parameter measurement.

7 Claims, 8 Drawing Sheets

Related U.S. Application Data

(60) Provisional application No. 63/157,364, filed on Mar. 5, 2021.

(58) Field of Classification Search
CPC .... A61B 5/145; A61B 5/02055; G16H 40/63; G16H 50/70
USPC ......................... 600/481, 483, 485, 490–499
See application file for complete search history.

(56) References Cited

U.S. PATENT DOCUMENTS

| | | |
|---|---|---|
| 6,475,153 B1 | 11/2002 | Khair et al. |
| 6,993,377 B2 | 1/2006 | Flick et al. |
| 7,286,875 B1 | 10/2007 | Park et al. |
| 7,544,168 B2 | 6/2009 | Nitzan |
| 7,787,946 B2 | 8/2010 | Stahmann et al. |
| 8,239,010 B2 | 8/2012 | Banet et al. |
| 8,308,649 B2 | 11/2012 | Holmstrom et al. |
| 8,761,853 B2 | 6/2014 | Thaveeprungsriporn et al. |
| 10,229,754 B2 | 3/2019 | Cronin et al. |
| 10,349,893 B2 | 7/2019 | Lee et al. |
| 10,413,197 B2 | 9/2019 | LeBoeuf et al. |
| 10,420,515 B2 | 9/2019 | Sinha et al. |
| 10,716,481 B2 | 7/2020 | LeBoeuf et al. |
| 10,729,338 B2 | 8/2020 | Wang et al. |
| 10,820,857 B2 | 11/2020 | Nasry |
| 11,154,208 B2 | 10/2021 | Nitzan |
| 11,324,411 B2 | 5/2022 | Sinha et al. |
| 11,445,982 B2 | 9/2022 | Lyman et al. |
| 11,534,070 B2 | 12/2022 | Tsutsumi et al. |
| 11,717,253 B2 | 8/2023 | Jones |
| 11,744,523 B2 * | 9/2023 | Sinha ..................... A61B 5/145 |
| | | 600/481 |
| 11,881,319 B2 | 1/2024 | Junnarkar |
| 2003/0163057 A1 | 8/2003 | Flick et al. |
| 2007/0066910 A1 | 3/2007 | Inukai et al. |
| 2008/0045818 A1 | 2/2008 | Wood et al. |
| 2008/0077025 A1 | 3/2008 | Delgado-Herrera et al. |
| 2009/0326386 A1 | 12/2009 | Sethi et al. |
| 2010/0168589 A1 | 7/2010 | Banet et al. |
| 2011/0066051 A1 | 3/2011 | Moon et al. |
| 2011/0077531 A1 | 3/2011 | Addison et al. |
| 2011/0224564 A1 | 9/2011 | Moon et al. |
| 2011/0245628 A1 | 10/2011 | Baker et al. |
| 2012/0029320 A1 | 2/2012 | Watson et al. |
| 2012/0179011 A1 | 7/2012 | Moon et al. |
| 2012/0190947 A1 | 7/2012 | Chon et al. |
| 2013/0171599 A1 | 7/2013 | Bleich et al. |
| 2013/0276785 A1 | 10/2013 | Melker et al. |
| 2013/0310656 A1 | 11/2013 | Lim et al. |
| 2013/0324859 A1 | 12/2013 | Park et al. |
| 2013/0345568 A1 | 12/2013 | Mestha et al. |
| 2014/0003454 A1 | 1/2014 | Kaemmerer et al. |
| 2014/0100485 A1 | 4/2014 | Linguraru et al. |
| 2014/0275854 A1 | 9/2014 | Venkatraman et al. |
| 2014/0278220 A1 | 9/2014 | Yuen |
| 2014/0303454 A1 | 10/2014 | Clifton et al. |
| 2015/0037937 A1 | 2/2015 | Park et al. |
| 2015/0080746 A1 | 3/2015 | Bleich et al. |
| 2015/0182132 A1 | 7/2015 | Harris et al. |
| 2015/0324977 A1 | 11/2015 | Magrath et al. |
| 2015/0379370 A1 | 12/2015 | Clifton et al. |
| 2016/0058375 A1 | 3/2016 | Rothkopf |
| 2016/0256117 A1 | 9/2016 | Baik et al. |
| 2016/0302674 A1 | 10/2016 | Moyer et al. |
| 2016/0360980 A1 | 12/2016 | Sinha et al. |
| 2017/0007137 A1 | 1/2017 | Hong et al. |
| 2017/0071516 A1 | 3/2017 | Bhagat et al. |
| 2017/0079533 A1 | 3/2017 | Robinson et al. |
| 2017/0238878 A1 | 8/2017 | Lading et al. |
| 2018/0110470 A1 | 4/2018 | Lee et al. |
| 2018/0146865 A1 | 5/2018 | Ortlepp |
| 2018/0177414 A1 | 6/2018 | Tokko et al. |
| 2018/0184983 A1 | 7/2018 | Petersen et al. |

| | | |
|---|---|---|
| 2018/0263513 A1 | 9/2018 | Qasem |
| 2018/0310891 A1 | 11/2018 | Fine et al. |
| 2019/0059753 A1 | 2/2019 | Chen et al. |
| 2019/0059825 A1 | 2/2019 | Baruch |
| 2019/0104953 A1 | 4/2019 | Narasimhan |
| 2019/0138846 A1 | 5/2019 | Durrleman et al. |
| 2019/0175120 A1 | 6/2019 | Huang |
| 2019/0357781 A1 | 11/2019 | Sinha et al. |
| 2020/0037956 A1 | 2/2020 | Kang et al. |
| 2020/0107763 A1 | 4/2020 | Antunes et al. |
| 2020/0196878 A1 * | 6/2020 | Bentzion ............... A61B 5/1118 |
| 2020/0297220 A1 | 9/2020 | Lu et al. |
| 2021/0345939 A1 | 11/2021 | Jumbe et al. |
| 2022/0280118 A1 * | 9/2022 | Sinha ................... A61B 5/0295 |
| 2023/0082362 A1 | 3/2023 | Varadan et al. |
| 2023/0125180 A1 | 4/2023 | Singh et al. |
| 2023/0148880 A1 | 5/2023 | Sinha |
| 2023/0165456 A1 | 6/2023 | Wada et al. |
| 2023/0200664 A1 | 6/2023 | Peters |
| 2023/0210386 A1 | 7/2023 | Naito et al. |
| 2023/0277130 A1 | 9/2023 | Khaleghimeybodi et al. |
| 2023/0293103 A1 | 9/2023 | Higuchi et al. |
| 2024/0041402 A1 | 2/2024 | Stevenson |
| 2024/0096507 A1 | 3/2024 | Junnarkar |
| 2024/0108303 A1 | 4/2024 | Tamborini et al. |
| 2024/0122491 A1 | 4/2024 | Lee et al. |
| 2024/0138687 A1 | 5/2024 | Balashov et al. |
| 2024/0188839 A1 | 6/2024 | Ito et al. |
| 2024/0298902 A1 | 9/2024 | John Archibald |
| 2024/0358326 A1 | 10/2024 | Dwarika et al. |
| 2024/0374219 A1 | 11/2024 | Mohammadi et al. |

FOREIGN PATENT DOCUMENTS

| | | |
|---|---|---|
| CN | 106236049 A | 12/2016 |
| EP | 2992820 A2 | 3/2016 |
| JP | 2016528981 A | 9/2016 |
| KR | 20160028093 A | 3/2016 |
| WO | 2014022906 A1 | 2/2014 |
| WO | 2015193551 A1 | 12/2015 |
| WO | 2024/081244 A1 | 4/2024 |
| WO | 2024/092014 A1 | 5/2024 |

OTHER PUBLICATIONS

"Clinical Validation of Tele-stethoscope System Digital", https://clinicaltrials.gov/ct2/show/study/NCT03596541, first posted Jul. 24, 2018.

"National Institute of Health and Nutrition Examination Survey (NHANES)", Health Tech/Blood Pressure Procedures Manual, May 2009.

"Non-invasive sphygmomanometers—Part 2: Clinical investigation of intermittent automated measurement type", International Standard, ISO 81060-2, Third edition Nov. 2018.

Alpert, Bruce , "The Accutension Stetho, an automated auscultatory device to validate automated sphygmomanometer readings in individual patients", Journal of Human Hypertension (2018) 32:455-459, Apr. 6, 2018, https://doi.org/10.1038/s41371-018-0053-2.

Elgendi, Mohamed , "Merging digital medicine and economics: Two moving averages unlock biosignals for better health", Diseases 6.1 (2018): 6. (Year: 2018).

Lai, Lillian S.W., et al., "Computerized Automatic Diagnosis of Innocent and Pathologic Murmurs in Pediatrics: A Pilot Study", Congenital Heart Dis. 2016;11:386-395.

Lee, Han-Wook , et al., "he periodic moving average filter for removing motion artifacts from PPG signals", International Journal ofControl, Automation, and Systems 5.6 (2007): 701-706. (Year: 2007).

Perpetuini, David , et al., "Multi-site photoplethysmographic and electrocardiogram for arterial stiffness and cardiovascular status assessment", Sensors 19.24 (2019): 5570. (Year: 2019).

Rojano, Juan F., "Singular value decomposition of the time-frequency distribution of PPG signals for motion artifact reduction", Int. J. Signal Process. Syst 4.6 (2016): 475-482. (Year: 2016).

(56)                References Cited

OTHER PUBLICATIONS

Scholze, A. , et al., "Increased arterial vascular tone during the night in patients with essential hypertension", Journal of Human Hypertension (2007) 21, 60-67. published online Oct. 5. [retrieved on Aug. 22, 2016] retrieved from the Internet : http://www.nature.com.

Stergiou, George S., et al., "A Universal Standard for the Validation of Blood Pressure Measuring Devices", Hypertension, Mar. 2018;71(3):368-374, doi: 10.1161/HYPERTENSIONAHA.117. 10237. Epub Jan. 31, 2018.

Stergiou, George S., et al., "Validation protocols for blood pressure measuring devices in the 21st century", J Clin Hypertens. 2018;20:1096-1099.

Sugita, Norihiro , et al., "Techniques for estimating blood pressure variation using video images", 37th Annual International Conference of the IEEE Engineering in Medicine and Biology Society (EMBC) Aug. 29, 2015.

Trafton, Anne , "In the blink of an eye, MIT neuroscientists find the brain can identify images seen for an as little as 13 milliseconds", MIT News, Jan. 16, 2014.

Vadrevu, Simhadri , et al., "A robust pulse onset and peak detection method for automated PPG signal analysis system", IEEE Transactions on Instrumentation and Measurement 68.3 (2018): 807-817. (Year: 2018).

Wang, Lu , et al., "Multi-Gaussian fitting for pulse waveform using weighted least squares and multi-criteria decision making method", Computers in biology and medicine 43.11 (2013): 1661-1672. (Year: 2013).

Wu, Hongiun , et al., "A New Automatic blood pressure kit auscultates for accurate reading with a smartphone", Medicine (2016) 95:32.

Dey, Jishnu , et al., "InstaBP: cuff-less blood pressure monitoring on smartphone using single PPG sensor", 2018 4th annual international conference of the IEEE engineering in medicine and biology society (EMBC). IEEE, 2018. ( Year: 2018).

Chan, et al., "Diagnostic performance of a smartphoneabased photoplethysmographic application for atrial fibrillation screening in a primary care setting", Journal of the American Heart Association 5.7 (2016): e003428. (Year: 2016).

Couceiro, et al., "Assessment of cardiovascular function from multi-Gaussian fitting of a finger photoplethysmogram.", Physiological measurement 36.9 (2015): 1801. (Year: 2015).

Couceiro, et al., "Characterization of surrogate parameters for blood pressure regulation in neurally-mediated syncope", 2013 35th Annual International Conference of the IEEE Engineering in Medicine and Biology Society (EMBC). IEEE, 2013. (Year: 2013).

Fedor, "Predicting health-related quality of life in early adulthood from individual differences in adolescent neurocognitive development", Diss. University of Pittsburgh, 2020. (Year: 2020).

Hamid, et al., "Methods of Extracting Feature from Photoplethysmogram Waveform for Non-Invasive Diagnostic Applications", International Journal of Online & Biomedical Engineering 16.9 (2020). (Year: 2020).

Reddy, et al., "Evaluation of objective distortion measures for automatic quality assessment of processed PPG signals for real-time health monitoring devices", Ieee Access 10 ( 2022): 15707-15745. (Year: 2022).

Rezaeisharif, "A Decision Support Model for the Necessity of Cardio-Angiography, A Result of Generalized Additive and logistic Regression Model", Journal of Biostatistics and Epidemiology (2021). (Year: 2021).

Tang, et al., "Synthetic photoplethysmogram generation using two Gaussian functions", Scientific Reports 10.1 (2020): 13883. (Year: 2020).

* cited by examiner

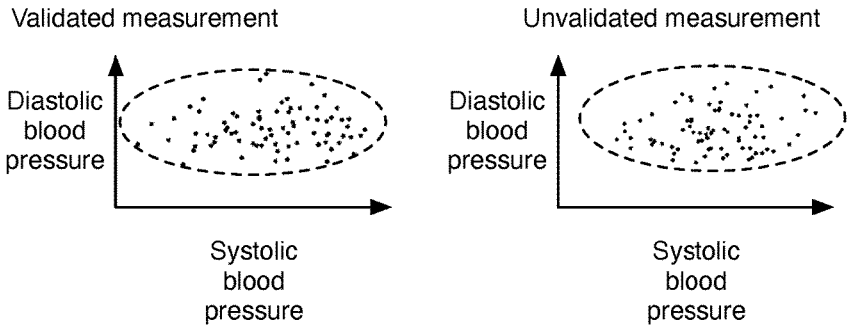
FIGURE 6
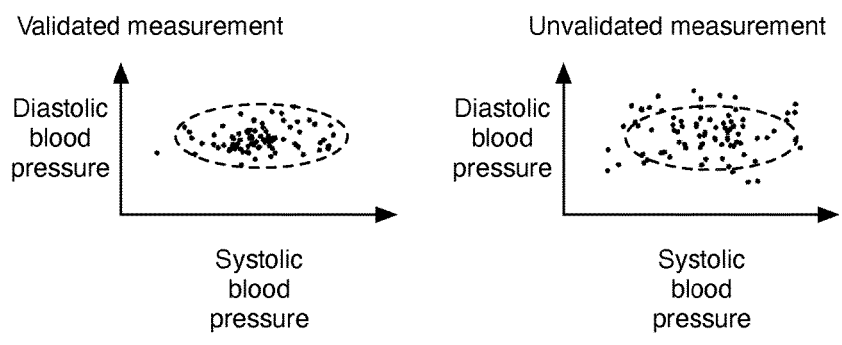
FIGURE 7
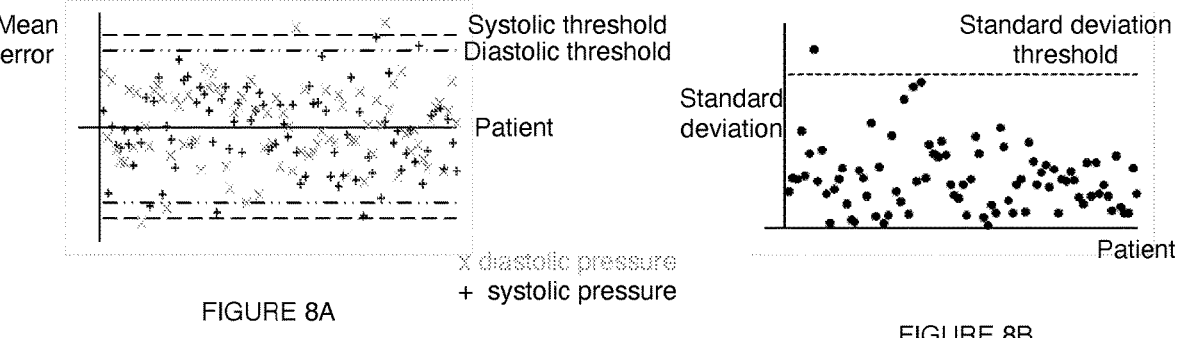
FIGURE 8A
FIGURE 8B

SYSTEM AND METHOD FOR VALIDATING CARDIOVASCULAR PARAMETER MONITORS

CROSS-REFERENCE TO RELATED APPLICATIONS

This application is a divisional of U.S. application Ser. No. 17/688,514, filed 7 Mar. 2022, which claims the benefit of U.S. Provisional Application No. 63/157,364, filed 5 Mar. 2021, each of which is incorporated in its entirety by this reference.

TECHNICAL FIELD

This invention relates generally to the cardiovascular parameter monitor field, and more specifically to a new and useful system and method in the cardiovascular parameter monitor field.

BRIEF DESCRIPTION OF THE FIGURES

FIGS. 6 and 7 are schematic representations of an exemplary scatterplots relating a diastolic and systolic blood pressure for a plurality of patients, where the test cardiovascular parameter monitor of FIG. 6 would likely be validated and the test cardiovascular parameter monitor of FIG. 7 would likely not be validated.

FIGS. 8A and 8B are schematic representations of examples of mean error (separately for systolic and diastolic blood pressure) and blood pressure standard deviation, respectively. The figures include examples of validation threshold for the respective test statistics.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
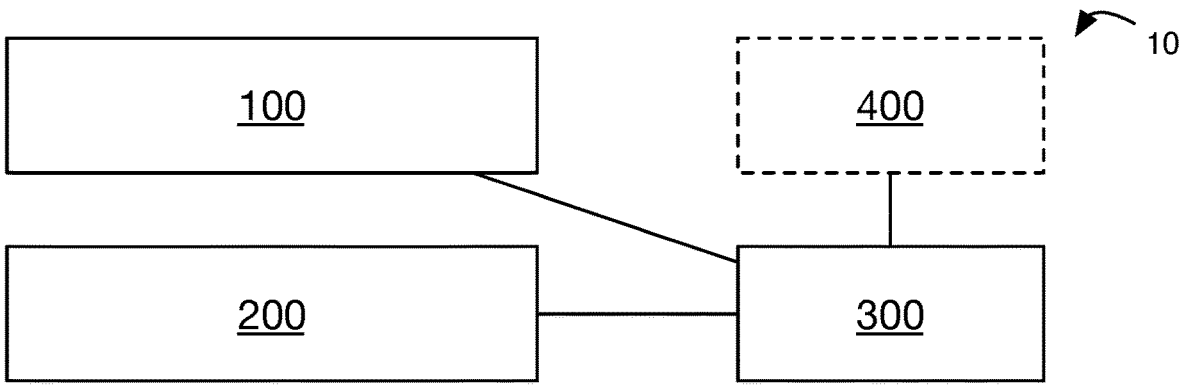
FIG. 1 is a schematic representation of the system.
Figure 2:
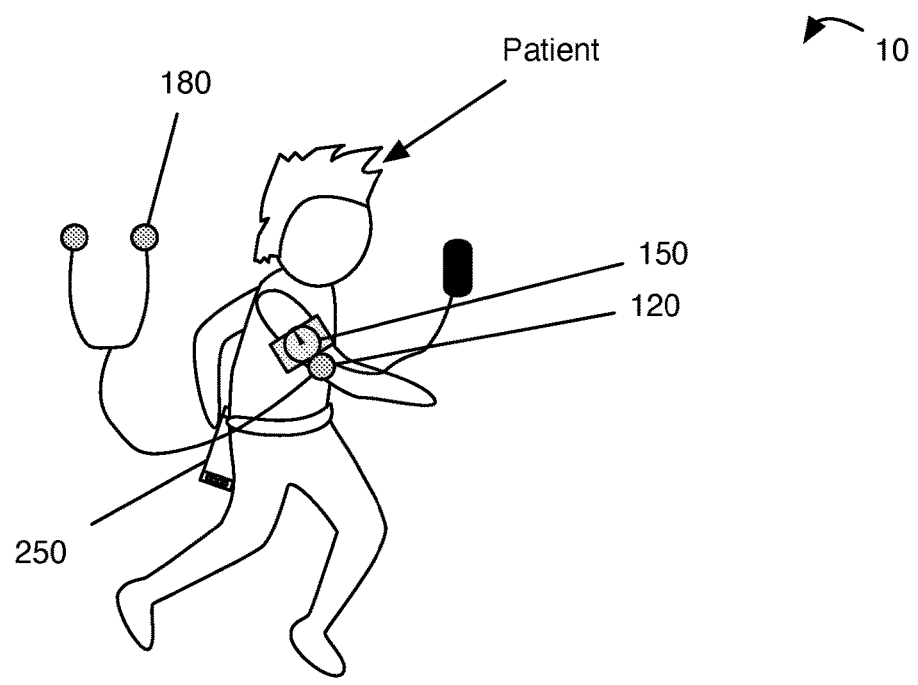
FIG. 2 is a schematic representation of an example of a patient using the system.

As shown in FIG. 1, the system 10 can include a validated cardiovascular parameter device 100, an unvalidated cardiovascular parameter device 200, and a computing system 300. The system can optionally include an auxiliary device 400 and/or any suitable components. In an illustrative example, as shown in FIG. 2, the validated cardiovascular parameter device can be an auscultatory device (e.g., a blood pressure cuff 120, a manometer 150, a stethoscope 180, etc.) and the unvalidated cardiovascular parameter device can be a photoplethysmometer 250 (e.g., a user device, a smart phone, a smart phone camera, a ring, etc.). However, any validated and/or unvalidated cardiovascular parameter devices can be used.

Figures 3, 4:
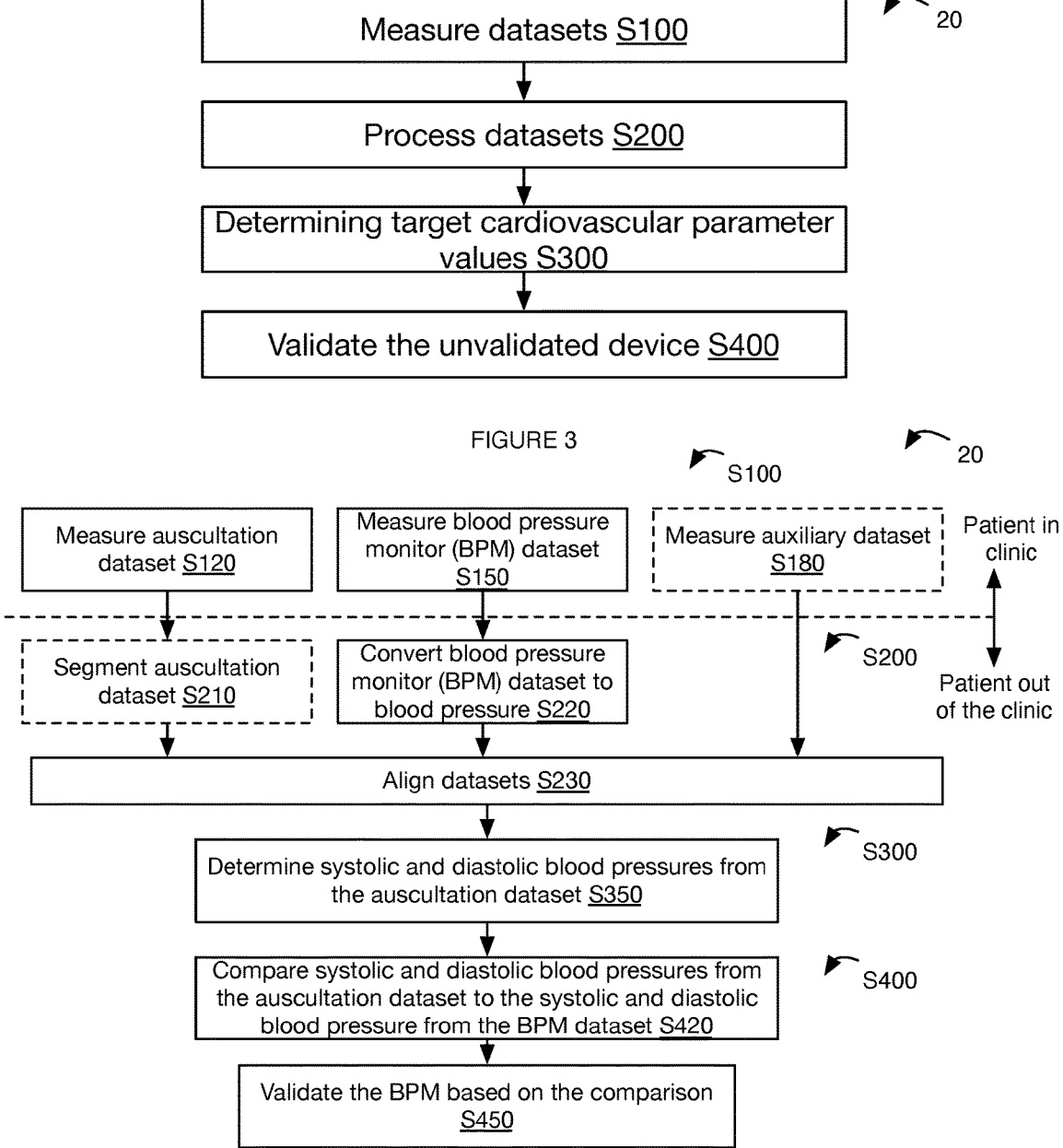
FIG. 3 is a schematic representation of the method.
FIG. 4 is a schematic representation of an exemplary embodiment of the method.

As shown in FIG. 3, the method 20 can include receiving datasets S100; processing the datasets S200; determining target cardiovascular parameters S300; and validating the test cardiovascular device S400. However, the method can additionally or alternatively include any suitable steps.

In an illustrative example as shown in FIG. 4, the method 20 can include measuring an auscultatory dataset and a plethysmogram dataset, aligning (e.g., temporally aligning) the auscultatory and plethysmogram datasets, transforming the plethysmogram dataset to a blood pressure, determining the systolic and diastolic blood pressure based on an audio dataset of the auscultatory dataset, comparing the systolic and diastolic blood pressure determined using the auscultatory and plethysmogram datasets, and validating the plethysmogram device used to measure the plethysmogram dataset based on the comparison. However, the method can otherwise be performed.

The system and method can be used with one or more patients. The number of patients used for the validation is preferably at least about 50 patients (e.g., 45, 50, 55, 60, 70, 75, 80, 85, 90, 100, 125, 150, 200, 300, 500, 1000, values or ranges therebetween, etc.). Each patient can be a member of a patient group (e.g., based on one or more patient characteristics) and/or include any suitable patient characteristics. The unvalidated cardiovascular parameter device is preferably validated for any patient and/or any unvalidated cardiovascular parameter device; however, the unvalidated cardiovascular parameter device can be validated (or invalidated) for one or more patient groups and/or particular patient characteristics, for particular unvalidated cardiovascular parameter devices (e.g., individual devices that are validated, specific generations of device, specific operating systems, specific models, etc.), and/or can otherwise validate (or invalidate) any suitable device(s). Examples of patient characteristics include: gender, family medical history, race, age, height, weight, physical fitness, job, medications, medical history, religion, and/or any suitable patient characteristics. The validation patient group preferably includes a representative variety of patients associated with different patient characteristics. In a first example, at least 30% of the patients can be male and at least 30% of the patients can be female. In a second example, a subset of patients (e.g., at least about 10 patients) can include calluses, scars, blisters, ulcerations, blemishes, corns, and/or other skin growths (e.g., from manufacturing work, for playing stringed instruments, etc.). In a third example, the validation patient group can include patients between 18 and 85 years of age. In a fourth example, the validation patient group can include a pediatric cohort (e.g., patients with ages 6 mo-2 years, 2-5 years, 5-12 years, 12-18 years, <18 years, etc.) such as with 10-30 patients. In a fifth example, the validation patient group can include at least a threshold number of patients (e.g., at least 50 patients) with a dark skin type (e.g., as defined by the Fitzpatrick Skin Type classification V, VI, etc.). In a sixth example, the validation patient group can include a subset of patients with hypertension, a subset of patients with hypotension, and a subset of patients with normal blood pressure. However, the validation patient group can include any suitable patients (e.g., exhibiting any combination of patient characteristics). Similarly, patients can be excluded from the validation patient cohort based on one or more exclusion criterion. Exemplary exclusion criteria include: pregnancy, breastfeeding, pre-existing conditions (e.g., aortic coarctation, arterial-venous malformation, occlusive arterial disease, antecubital bruit, pericardial tamponade, restrictive cardiomyopathy, constrictive pericarditis, etc.), poor auscultation measurements, vascular implants, allergies (e.g., allergic to pharmacological stressor such as nitroglycerine), medications, and/or any suitable exclusion criteria.

2. Benefits

Variations of the technology can confer several benefits and/or advantages.

First, the inventors have found that methods of validating blood pressure monitor readings (e.g., having two simultaneous auscultation readings performed by individuals in the same room) can be limited by human error. For example, instrument reading errors (e.g., parallax effects), auditory perception, or distractions can lead to results invalidating or not validating a blood pressure monitor (or other cardiovascular parameter device) that could have been validated in the absence of these errors. The inventors have found that using digital auscultation and synchronizing the data readings (e.g., between validated and unvalidated devices) can help overcome these limitations and can improve the validation of blood pressure monitors (and/or other cardiovascular parameter measurement devices). Similarly, these techniques can enable blood pressure monitor validation to be performed outside of a health care clinic.

However, variants of the technology can confer any other suitable benefits and/or advantages.

As used herein, "substantially" or other words of approximation (e.g., "about," "approximately," etc.) can be within a predetermined error threshold or tolerance of a metric, component, or other reference (e.g., within 0.001%, 0.01%, 0.1%, 1%, 5%, 10%, 20%, 30%, etc. of a reference), or be otherwise interpreted.

3. System

As shown in FIG. 1, the system 10 can include a validated cardiovascular parameter device 100, an unvalidated cardiovascular parameter device 200, and a computing system 300. The system can optionally include an auxiliary device 400 and/or any suitable components. The system preferably functions to validate (or invalidate), such as to determine a validity or accuracy of, the unvalidated cardiovascular parameter device, but can otherwise function. The cardiovascular parameter is preferably blood pressure. However, the cardiovascular parameter can additionally or alternatively include: arterial stiffness, stroke volume, heart rate, blood volume, pulse transit time, phase of constriction, pulse wave velocity, heart rate variability, blood pressure variability, medication interactions (e.g., impact of vasodilators, vasoconstrictors, etc.), cardiovascular drift, cardiac events (e.g., blood clots, strokes, heart attacks, etc.), cardiac output, cardiac index, systemic vascular resistance, oxygen delivery, oxygen consumption, baroreflex sensitivity, stress, sympathetic/parasympathetic tone, blood composition, metabolites, metabolic markers (e.g., insulin, glucose, glycosylated hemoglobin (Hb-A1c), triglyceride, cholesterol, cholesterol ratio, free fatty acid, lipids, etc.), vascular changes (e.g., due to plaque, lesions, etc.) and/or any suitable cardiovascular parameters and/or properties.

The validated cardiovascular parameter device functions to measure a validated dataset that can serve as a source of truth for the cardiovascular parameter of the patient(s). The validated dataset can be a direct or indirect (e.g., be transformed to) measurement of the cardiovascular parameter. The validated cardiovascular parameter device is preferably a digital device which can facilitate storage of the measured values, but can additionally or alternatively be analog (e.g., connect to an analog to digital converter to record values, measurements recorded using a camera or other image capture system, measurements recorded by a human, etc.). The validated cardiovascular parameter device preferably measures data a frequency of at least about 10 Hz, but can measure data less frequently than 10 Hz.

The validated cardiovascular parameter device is preferably an auscultatory device, but can include a catheter (e.g., arterial catheter) and/or any suitable validated blood pressure monitor (e.g., validated as disclosed below, validated by a testing body, validated by a government entity, etc.), and/or any suitable validated monitor. As shown for example in FIG. 2, the auscultatory device can include a sphygmomanometer (e.g., blood pressure cuff), a stethoscope (e.g., a digital stethoscope), and a data recorder. The data recorder can record the pressure applied by the blood pressure cuff (e.g., the instantaneous pressure as the cuff is inflated and deflated, a manometer, a pressure sensor, pressure recorder, etc.), an audio signal from the stethoscope, and/or any suitable data. In this specific example, the pressure readings are preferably accurate to at least 0.1 mmHg, but can be accurate to a pressure greater than 0.1 mmHg (such as 1 mmHg, 3 mmHg, 10 mmHg, etc.) and/or to ay suitable accuracy.

The sphygmomanometer is preferable automatic, but can be manual and/or otherwise be operable. A deflation rate of the sphygmomanometer is preferably at most about 5 mmHg/s (e.g., 5 mmHg/s, 4 mmHg/s, 3 mmHg/s, 2 mmHg/s, 1 mmHg/s, 0.5 mmHg/s, 0.1 mmHg/s, values or ranges therebetween, etc.), which can enable adequate deflation periods to be achieved (e.g., facilitating detection of Korotkoff sounds). However, the deflation rate can be greater than about 5 mmHg/s. The deflation time is preferably at least about 20 s (e.g., 20 s, 25 s, 30 s, 45 s, 60 s, etc.), but can be less than about 20 s. The total inflation and deflation cycle time (e.g., from 0 pressure to inflation to deflation back to 0 pressure) is preferably at least about 30 s (e.g., 30 s, 35 s, 40 s, 45 s, 60 s, 90 s, 120 s, etc.), but can be less than about 30 s.

The sphygmomanometer size preferably matches a patient arm size. However, the sphygmomanometer size can be constant and/or can otherwise be selected.

In an illustrative example, a manometer can record the pressure readings for the sphygmomanometer at a frequency that is at least about 10 Hz (e.g., 8 Hz, 9 Hz, 10 Hz, 20 Hz, 50 Hz, 100 Hz, 200 Hz, etc.) and a digital stethoscope can contemporaneously (e.g., during sphygmomanometer inflation and deflation, with pressure readings, etc.) record a digital audio signal with a frequency of at least about 10 kHz (e.g., 9 kHz, 10 kHz, 15 kHz, 20 kHz, 25 kHz, 30 kHz, 40 kHz, 48 kHz, 50 kHz, 80 kHz, etc.). Having the digital audio signal read out at a higher rate than the pressure readings can be beneficial in achieving a target cardiovascular parameter (e.g., blood pressure) reading using the validated cardiovascular parameter device. In this specific example, for instance, the combination of the manometer reading and the audio data set can enable a blood pressure reading accuracy of about 1 mmHg. However, the readout frequencies can be the same, the audio signal can have a lower frequency than the pressure signal, and/or the frequencies can otherwise be related.

The unvalidated cardiovascular parameter device functions to acquire an unvalidated dataset related to a patient's cardiovascular parameter(s). The unvalidated cardiovascular parameter device can be never previously validated, can previously have been validated (e.g., a validation state has expired such as due to an elapsed time since a prior validation), can previously have been invalidated, can be validated for one or more types of cardiovascular parameters but not others, be validated in certain jurisdictions, and/or can otherwise be a device that is to be validated. The unvalidated dataset is preferably compared to the validated dataset to validate (or invalidate) the unvalidated cardiovascular parameter device. The unvalidated dataset can be a direct or indirect (e.g., be transformed to) measurement of the cardiovascular parameter. The unvalidated cardiovascular parameter device is preferably digital, but can be analog. The unvalidated cardiovascular parameter device preferably measures data a frequency of at least about 10 Hz, but can measure data less frequently than 10 Hz. In a specific example, the unvalidated dataset can be a pulse waveform dataset. However, any suitable dataset can be used.

The validated and unvalidated cardiovascular parameter devices can contact (e.g., touch), be mounted to (e.g., using adhesive, using glue, applying pressure, etc.), and/or otherwise be coupled to the patient. The validated and unvalidated cardiovascular parameter device are preferably coupled to different limbs or appendages of the patient, which can be beneficial for avoiding crosstalk, contamination, artifacts, or other effects of having two devices for measuring the same or similar cardiovascular parameter in the same blood flow path. For example, the validated cardiovascular parameter device can be mounted to an arm region of the patient (e.g., an upper arm region of a first arm of a patient) and the unvalidated cardiovascular parameter device can be contacted to a finger of the patient's other arm. However, the validated and unvalidated cardiovascular parameter devices can be coupled to the same limbs of the patient (such as the same arms, an arm and a leg, an arm and a foot, an arm and a chest, an arm and an artery, etc.), coupled to a core of the patient (e.g., torso, trunk, etc.), and/or otherwise be coupled to the patient.

Examples of unvalidated cardiovascular parameter devices include: blood pressure monitors (e.g., palpatory, auscultatory, oscillometric, CNAP, pulse wave velocity, etc.), plethysmometer (e.g., photoplethysmometers such as a pulse oximeter, user device, smart phone, dedicated instrument, camera, camcorder, etc.), contactless blood pressure monitors, and/or any suitable devices.

The optional auxiliary device function to acquire one or more auxiliary datasets that can be correlated with the validated and/or unvalidated datasets. The auxiliary datasets are preferably acquired contemporaneously or simultaneously with the validated or unvalidated datasets, but can additionally or alternatively be acquired delayed relative to the validated and/or unvalidated datasets, and/or the auxiliary datasets can be acquired with any suitable timing. Examples of auxiliary datasets include measurements of: electrical activity (e.g., using electroencephalography (EEG), using electrocardiography (ECG or EKG), etc.), blood oxygenation, glucose level, respiratory rate, body temperature, blood stroke volume, imaging (e.g., using magnetic resonance imaging (MRI), computed tomography (CT), positron emission tomography (PET), ultrasound, radionuclide, x-rays, etc.), and/or any suitable measurements. The auxiliary device can be any suitable device configured to measure the auxiliary dataset and/or any suitable device (e.g., an ECG machine, a glucose monitor, an oximeter, etc.). The auxiliary device preferably measures data a frequency of at least about 10 Hz, but can measure data less frequently than 10 Hz.

The computing system functions to perform one or more steps of the method. The computing system can be local (e.g., integrated into one or more of the unvalidated cardiovascular parameter devices, the validated cardiovascular parameter devices, and/or the auxiliary device; a separate computing station; etc.), remote (e.g., cloud computing system, server, database, etc.), and/or distributed in any suitable manner.

4. Method

As shown in FIG. 3, the method can include receiving datasets; processing the datasets; comparing target cardiovascular parameters; and validating the test cardiovascular device. However, the method can additionally or alternatively include any suitable steps. However, the method can otherwise be performed. The method preferably functions to validate (e.g., for a single patient, for a group of patients, for a patient population, for any patient, for a given device, for a given device class, for a given method of operating devices, etc.) an unvalidated cardiovascular parameter device. The method is preferably performed using a system as described above, but can be performed by any suitable system.

Steps of the method are preferably able to be delayed relative to one another (e.g., by minutes, hours, days, weeks, months, or longer), but can be performed without a delay (e.g., a delay of less than a minute, in real-time, etc.) and/or with any suitable timing. The method or steps thereof can be performed in a clinical environment (e.g., a doctor's office, pharmacy, etc.), in a patient's home, in a data processing center, distributed between locations (e.g., datasets can be acquired while patients are in a clinical environment and processed after the patients leave the clinical environment), and/or in any suitable location(s). In an exemplary embodiment, only S100 is performed while the patient is present (e.g., within a clinic). For example, an auscultation and plethysmogram datasets can be measured with the patient present (e.g., in a clinic, at a first time, etc.), while the systolic and diastolic blood pressure for the patient can be determined without the patient present (e.g., at a second time after the first time, where the second time can be minutes, hours, days, weeks, etc. after the first time). However, the patient(s) can additionally or alternatively be present (e.g., in a clinic) or absent for S200, S300, S400, and/or any suitable steps.

The method is preferably applied to patients with known characteristics and/or who are members of predetermined patient populations. However, the method can be applied to any suitable patients. The method can include determining patient characteristics (e.g., by measuring them, using a survey, by accessing a patient health history, etc.). The method can include selecting one or more patients. The patients can be selected based on patient characteristics (e.g., to ensure that a representative number of patients with particular characteristics are measured, where the representative number can reflect a characteristics distribution in a broader community, exclusion criteria such as to exclude one or more patient, etc.). However, the patients can otherwise be selected.

Figures 12A, 12B, 12C, 12D:
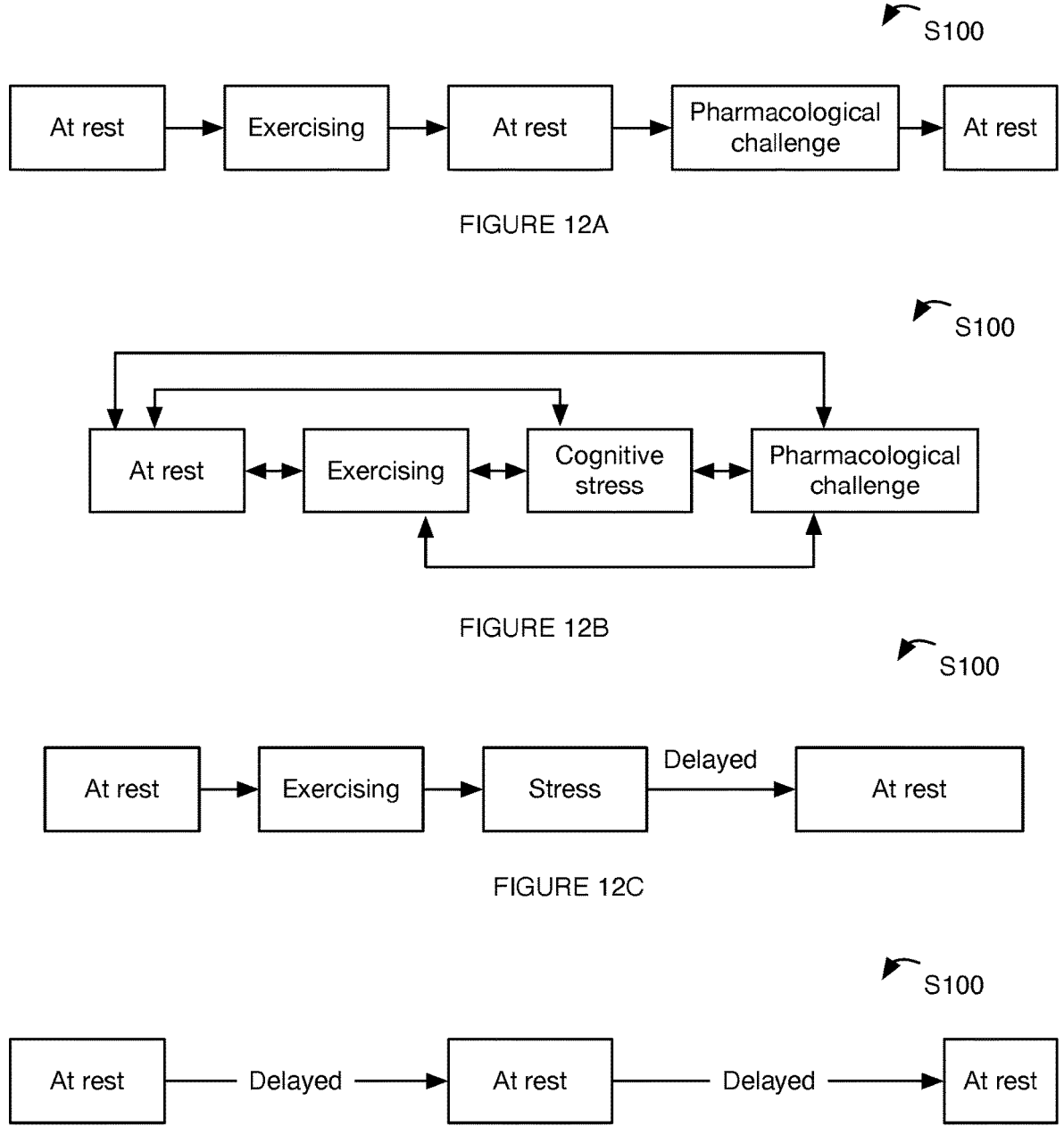
FIGS. 12A-12D are schematic representations of exemplary conditions a patient's cardiovascular parameter(s) are measured in. Conditions can occur in any order and can immediately follow one another, have a delay (e.g., as labeled in FIG. 12C and FIG. 12D, but can apply to any sequence of conditions), and/or can occur with any timing.

The method preferably includes performing at least S100 through S300 for each patient of a plurality of patients. The steps are preferably performed in the same manner for each patient (e.g., using the same validated and unvalidated cardiovascular parameter device), but can be performed in different manners (e.g., using different validated and unvalidated cardiovascular parameter device for each patient such as using a patient specific device). The method is preferably repeated a predetermined number of times for each patient, where the predetermined number can be once, twice, thrice, 5 times, 10 times, 20 times, 100 times, and/or any suitable number of times. The predetermined number of times can be performed on the same or different days (e.g., once a visit for a total of a predetermined number of visits, a predetermined number of times each visit, etc.). The measurements can be performed with the patient(s) (e.g., repeated measurements for one patient, measurements on each patient, etc.) in the same or different conditions. Examples of conditions can include: physical activity level (e.g., exercise such as isometric exercise, isotonic exercise, etc.), medication (e.g., pharmacological challenge such as using nitroglycerin), sitting, standing, sleeping, time of day, at rest, pain test (e.g., hot water immersion, cold water immersion, cold pressor test, etc.), meditation (e.g., deep breathing exercises), cognitive stress (e.g., sleep deprivation; stress task such as Portland arithmetic stress task, Montreal imaging stress task, etc.; etc.), and/or any suitable conditions. The measurement conditions can be performed in a continuous design (e.g., on the same day, within a threshold time such as 1 hour, without removing and replacing a validated cardiovascular parameter device, without removing and/or replacing an unvalidated cardiovascular parameter device, etc.), in an interrupted design (e.g., with a break between conditions; with a threshold amount of time spent between conditions such as 1 min, 5 min, 10 min, 30 min, 1 hour, 1 day, 1 week, 1 month, values or ranges therebetween, etc.; without removing and replacing a validated cardiovascular parameter device; without removing and/or replacing an unvalidated cardiovascular parameter device: etc.), a combination of continuous and interrupted design (e.g., test a stress condition against rest, compare stress conditions in the same siting, compare stress conditions in different sittings, etc.) and/or using any suitable design. In a first specific example (as shown for instance in FIG. 12A), the method (e.g., steps S100, S200, S300, S400, etc.) can be performed (e.g., for each patient) a predetermined number of times while the respective patient is at rest, a predetermined number of times while the respective patient performs an exercise (e.g., an isometric exercise), a predetermined number of times while the respective patient returns to (e.g., is at) rest, a predetermined number of times while the respective patient undergoes a pharmacological challenge, and/or a predetermined number of times while the respective patient returns to rest (e.g., as the pharmacological challenge is removed from their system). In a second illustrative example, each patient's cardiovascular parameter(s) can be measured in a first condition (e.g., a predetermined number of times while the patient is in the first condition) and in a second condition (e.g., different from the first, for the same or a different predetermined number of measurements). In a third illustrative example (as shown for instance in FIG. 12B), each patient's cardiovascular parameter(s) can be measured in an at rest, an exercise, a cognitive stress, and/or a pharmacological challenge condition. In a fourth illustrative example (as shown for instance in FIG. 12C), each patient's cardiovascular parameter(s) can be measured in an at rest, exercising, and/or stressed conditions; where the patient's cardiovascular parameters can be measured a plurality of times with delays between the conditions (e.g., repeating the sequence of measurement on consecutive days, repeating the sequence of measurements on different days, measuring different conditions of different days, performing measurements at different times of day, etc.). In a fifth illustrative example (as shown for instance in FIG. 12D), a patient's cardiovascular parameter(s) can be measured in the same condition across a plurality of times (e.g., different days, different times of day, in different settings, etc.). However, each patient's cardiovascular parameters can be measured in a single condition, in a different condition for different instances of the method (e.g., a first condition for a first visit to a clinic and a second condition for a second visit to a clinic), and/or the patient's cardiovascular parameters can be determined for any suitable condition(s).

Figure 5:
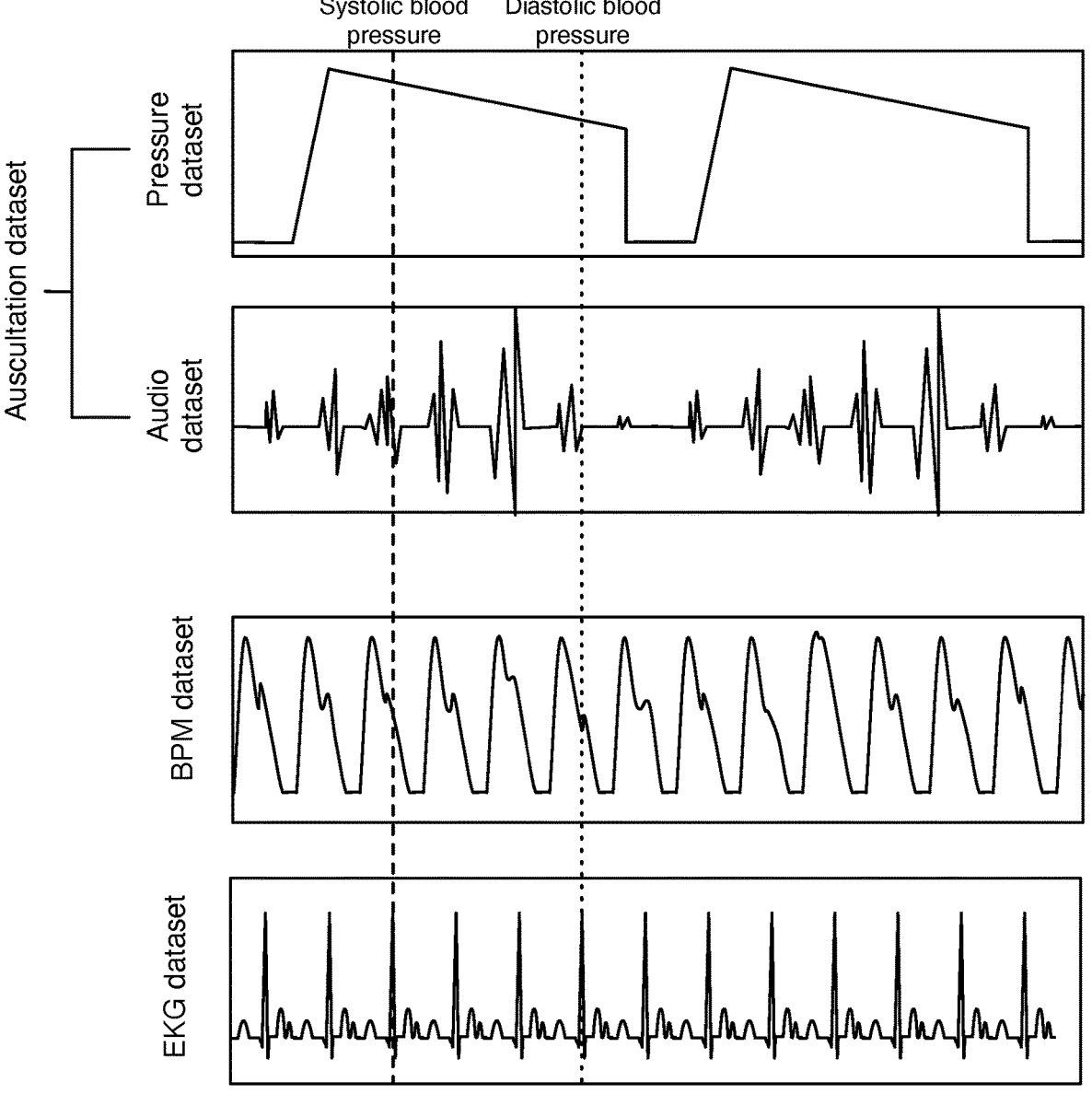
FIG. 5 is a schematic representation of an exemplary aligned datasets.

Measuring the datasets S100 functions to measure a validated and an unvalidated cardiovascular parameter dataset. S100 can additionally or alternatively measure an auxiliary dataset, and/or any suitable dataset(s). S100 is preferably performed in situ (e.g., while a patient is in a clinic, test facility, etc.), but can be performed ex situ (e.g., while a patient is not in a clinic, test facility, etc. such as to avoid a "white-coat" effect), and/or in any suitable location or situation. The datasets are preferably measured contemporaneously or simultaneously, but can be measured sequentially (e.g., unvalidated dataset before a validated dataset, validated dataset before an unvalidated dataset, etc.), at predetermined times, and/or with any suitable timing. The datasets can be measured synchronously (e.g., with the same frequency such that each datum is associated with the same time stamps, with a multiple of a common frequency so that datum align with the same time stamp, such that a reference datum is acquired at the same time stamp, synchronized to a common clock such that data acquisition for different datasets is initiated substantially simultaneously with respect to a data acquisition frequency of the data recording devices, etc.) or asynchronously (e.g., with different frequencies, without intentionally measuring datum at a common time stamp, etc.). Each dataset is preferably a function of time (e.g., as shown for example in FIG. 5, the datasets can measure a change in a cardiovascular parameter or measured quantity such as acoustic signal, pressure signal, pressure waveform, electrical signal, blood pressure, etc. with respect to time). However, the datasets can additionally or alternatively be a function of any suitable variable (e.g., position such as body region of the patient being measured, patient condition, etc.).

S100 can include: measuring a validated cardiovascular parameter dataset S120, measuring an unvalidated cardiovascular parameter dataset S150, measuring an auxiliary dataset S180, and/or any suitable steps.

The validated dataset is preferably measured using the validated cardiovascular parameter device, but can be measured using any suitable device. The unvalidated dataset is preferably measured using the unvalidated cardiovascular measurement device, but can be measured using any suitable device. The auxiliary dataset is preferably measured using the auxiliary device, but can be measured using ay suitable device.

In an illustrative example, a validated dataset can be an auscultatory dataset that includes a pressure dataset (e.g., associated with a pressure applied by a blood pressure cuff) and an audio dataset (e.g., associated with a stethoscope such as measuring the sound of blood flow within a patient's artery particularly but not exclusively as the pressure is increased and/or decreased). However, the validated dataset can include any suitable data. In an illustrative example, an unvalidated dataset can include a pulse waveform (e.g., a plethysmometer dataset). In an illustrative example, an auxiliary dataset can include an ECG dataset. However, any suitable datasets can be used.

S100 can include storing the datasets (e.g., to a database, to a memory cache, etc.), where the datasets can be retrieved between the time of their measurement and the performance of one or more steps of the method, between separate instances of the method (such as to compare the results across time elapsed between method instances), between separate conditions, and/or with any suitable timing. The datasets can be stored unprocessed or processed (e.g., processed according to S200, including annotations or other markings indicating target cardiovascular parameters, etc.).

In some variants, one or more datasets (particularly but not exclusively unvalidated datasets) can be measured as disclosed in U.S. patent application Ser. No. 16/538,361 filed 12 Aug. 2019 titled "METHOD AND SYSTEM FOR ACQUIRING DATA FOR ASSESSMENT OF CARDIO-VASCULAR DISEASE" incorporated in its entirety by this reference. However, the datasets can otherwise be measured.

Processing the datasets S200 functions to process (e.g., transform, denoise, align, etc.) one or more of the validated, unvalidated, and/or auxiliary datasets. S200 is preferably performed after S100 (e.g., after the complete dataset has been acquired), but can be performed during S100 (e.g., as the datasets are acquired, as a datum is measured, etc.). The datasets can be processed in the same or different manners. Examples of processes performed on datasets include: transformations S240 (e.g., scaling, shifting, rotating, changing basis such as using a Fourier Transform, etc.), segmenting datasets S210, converting measurements to cardiovascular parameters S220 (e.g., as disclosed in U.S. patent application Ser. No. 17/061,114 filed 1 Oct. 2020 entitled "METHOD AND SYSTEM FOR DETERMINING CAR-DIOVASCULAR PARAMETERS" incorporated in its entirety by this reference), aligning datasets S230 (e.g., aligning in time), resampling datasets (e.g., upsampling, downsampling, interpolating, extrapolating, expanding compressing, decimating, etc.), correcting for artefacts introduced by the dataset measurements (e.g., correcting for an effect of an inflated cuff on a blood pressure reading), filtering datasets (e.g., bandpass filtering, longpass filter, shortpass filter, notch filtering, etc. such as to reduce or remove a background), detecting outliers (e.g., auscultation data where one or more Korotkoff sounds are inaudible, unusual changes in blood pressure for a patient such as increased blood pressure during a pharmacological challenge expected to decrease blood pressure, etc.), and/or any suitable processing steps.

S200 (and/or subsequent steps) are preferably performed post-hoc (e.g., using post-hoc analysis, after a patient has left the clinic, when a patient is not in a testing center, etc.), but can be performed ad hoc (e.g., as needed), ex ante (e.g., a predicted patient cardiovascular parameter), concurrently with S100 (e.g., while the patient is in the clinic), and/or with any suitable timing. In a specific example, a systolic and a diastolic blood pressure can be determined from the validated cardiovascular parameter dataset (e.g., validated auscultation dataset) separately after the measurement is completed (which can be beneficial for improving an accuracy of the measurement by decreasing a risk of human measurement, determination, etc. error). However, the processing can be performed with any suitable timing. S200 can be performed with any suitable delay after S100 (e.g., 1 minute, 5 minutes, 10 minutes, 30 minutes, 1 hour, 2 hours, 4 hours, 6 hours, 8 hours, 12 hours, 24 hours, 30 hours, 36 hours, 48 hours, 72 hours, 96 hours, 120 hours, 1 week, 2 weeks, 4 weeks, 1 month, 2 months, 4 months, 6 months, 12 months, >12 months, <1 minute) and/or simultaneously with S100 (e.g., within <1 minute of performing S100).

In variants of processing the datasets, one or more datasets can be segmented into heart beats (e.g., individual heart beats, groups of heart beats, etc.). The datasets can be segmented based on an auxiliary dataset (e.g., an EKG dataset, where a QRS complex or other segment can be associated with a heartbeat), based on a frequency of signal detection, and/or otherwise segment the datasets. In a second variant of processing the datasets, a dataset (e.g., an audio dataset of an auscultatory dataset) can be segmented using a peak detection or peak finding algorithm, where the peak detection or peak finding can be performed in the time or frequency domain. In a specific example of the second variant, processing the dataset can include using a sliding window Fourier Transform to identify peaks in the audio dataset. However, the datasets can otherwise be segmented.

Figure 11:
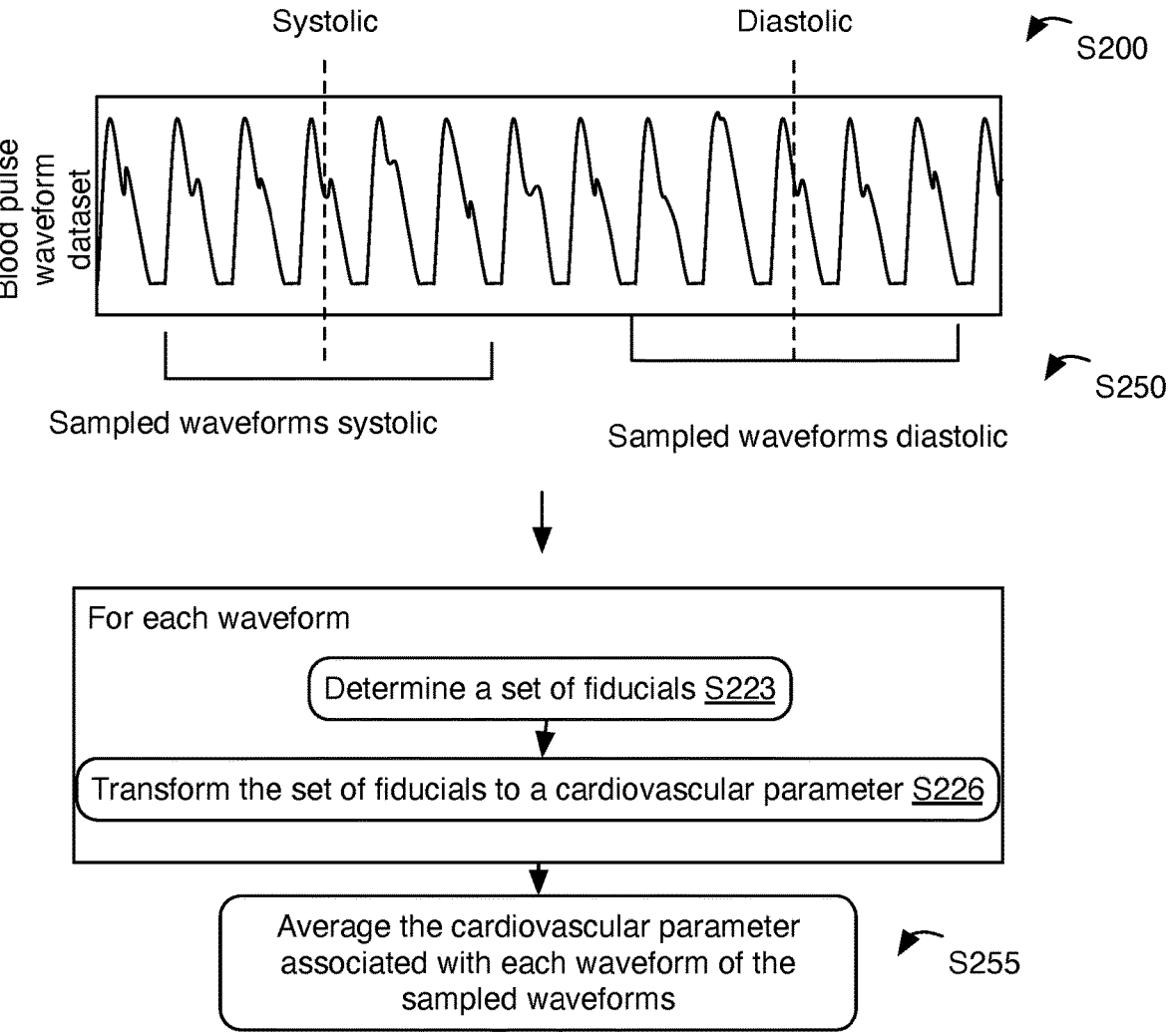
FIG. 11 is a schematic representation of an example of sampling a blood pulse waveform dataset and converting each blood pulse waveform (e.g., of the sample) to a cardiovascular parameter.

In some variants, the segments of datasets can be grouped S250. A group can be used to average data (e.g., some or all waveforms or associated cardiovascular parameter within a group can be averaged), to label data (e.g., with a condition), to compare to other datasets (e.g., to combine or compare data between patients), and/or can otherwise be used. For instance, the segments can be grouped into analyzed and unanalyzed datasets, into associated inflation-deflation periods, into groups based on measurement condition (e.g., rest, exercise, pharmacological challenge, etc.), and/or can otherwise be grouped. As an illustrative example (as shown for instance in FIG. 11), data (e.g., waveforms) within about ±5 s of a systolic or diastolic blood pressure can be grouped, where cardiovascular parameters determined from said waveforms can be combined 5255 (e.g., averaged) to determine a cardiovascular parameter for the waveform. In a variant of this illustrative example, a number of waveforms can be grouped around the systolic and/or diastolic blood pressures. The number of waveforms can be constant (e.g., 1, 2, 3, 4, 5, 6, 7, 8, 9, 10, >10), depend on a patient's pulse (e.g., more waveforms can be included for higher pulse, fewer waveforms can be included for higher pulse, more waveforms can be included for lower pulse, fewer waveforms can be included for lower pulse, the number of waveforms can depend on the patient's pulse, etc.), depend on a patient device, depend on the unvalidated cardiovascular parameter device, depend on a measurement condition (e.g., rest, exercise, pharmacological challenge, etc.), and/or any number of waveforms can be used and/or can depend on any suitable information.

In variants, processing a dataset (particularly but not exclusively an unvalidated dataset) can include transforming the dataset to a cardiovascular parameter dataset (e.g., a validated dataset can be transformed to a validated cardiovascular parameter dataset, an invalidated dataset can be transformed to an unvalidated cardiovascular parameter dataset, etc.). In a specific example of transforming the dataset, transforming the dataset can include any suitable step or steps as disclosed in U.S. patent application Ser. No. 17/061,114 filed 1 Oct. 2020 entitled "METHOD AND SYSTEM FOR DETERMINING CARDIOVASCULAR PARAMETERS," which is incorporated in its entirety by this reference. For instance, an unvalidated dataset (e.g., a wave pulse dataset) can be converted to an (unvalidated)

blood pressure dataset by extracting a set of fiducials S223 (e.g., fit parameters, zeros of derivatives, frequency components, etc. such as an amplitude, mean, standard deviation, etc. for a plurality of gaussians used to fit the waveform) from each waveform (e.g., each waveform to be analyzed) and transforming the set of fiducials to a blood pressure S226 (e.g., based on a cardiovascular manifold that relates vessel changes to a combination of the set of fiducials). However, processing the dataset can include any suitable step.

However, processing the dataset can include any suitable step(s).

Determining target cardiovascular parameters S300 functions to determine when target cardiovascular parameters are achieved in the validated dataset. The target cardiovascular parameter can include, for example, a systolic blood pressure, a diastolic blood pressure, a pulse pressure, pulse pressure relaxation, mean arterial pressure, mean blood pressure, pulse excitability, jugular venous pressure, portal venous pressure, critical closing pressure, pulse, compliance, vascular resistance, and/or perfusion. However, any suitable target cardiovascular parameter can be used. The target cardiovascular parameter(s) can be determined manually (e.g., by a health care worker, by a trained diagnostician, etc.) and/or automatically. For example, the target cardiovascular parameters can be determined using machine learning (e.g., neural network, convolutional neural network, recurrent neural network, etc.) that is trained to determine the target cardiovascular parameters from the validated dataset. The time associated with each target cardiovascular parameter is preferably stored, but can otherwise be manipulated. Each time unit can be associated with a specific heartbeat (e.g., a peak, trough, or other predetermined characteristic in the auxiliary dataset; a peak, trough, zero, FFT timing, etc. of an audio dataset; etc.), with a specific time, and/or be otherwise associated. In an illustrative example, when a time is identified with a target cardiovascular parameter, the time can be locked to a peak in the audio dataset (e.g., an FFT or Fourier transform peak of the audio dataset; spectrum of the audio dataset; peak, trough, zero, etc. of an audio dataset; etc.) and/or EKG dataset. However, the time can lock on to any suitable time.

In an illustrative example, the target cardiovascular parameters can be determined based on Korotkoff sounds S350 (e.g., phase I for systolic blood pressure, phase IV or V for diastolic blood pressure). For instance, the systolic blood pressure can be determined from an audio dataset (e.g., of an auscultatory dataset) based on the start of (e.g., the first heartbeat) turbulent flow as heard (or otherwise determined) in the audio dataset, where the associated time can be identified (for comparing with the other datasets such as the systolic blood pressure can be the value of the pressure dataset measured at or near the identified time, $1^{st}$ Korotkoff sound is detected, etc.). Similarly, the diastolic blood pressure can be identified from the audio dataset based on (the heartbeat) when the turbulent flow disappears (e.g., is no longer heard in the audio dataset such as the diastolic blood pressure can be the value of the pressure dataset measured at or near the identified time when turbulence is no longer heard, $4^{th}$ or $5^{th}$ Korotkoff sound is detected, etc.). In variations, two or more diagnosticians can determine the systolic and diastolic blood pressures by listening to the audio datasets and identifying the Korotkoff sounds associated with the blood pressure. When the diagnosticians identify a sound or heartbeat associated with each blood pressure, the time can lock to a nearest peak, trough, zero, or other point associated with the sound or heartbeat, which can facilitate reproducible timing and/or reading of the target cardiovascular parameters. In a second variation, artificial intelligence (e.g., a machine learning algorithm, neural network, etc.) can be used to detect the Korotkoff sounds. In a third variation, Korotkoff sounds can be detected based on a Fourier analysis (e.g., FFT, moving window Fourier analysis, etc.) of the audio dataset (e.g., to detect an onset of turbulent blood flow within the audio dataset, to detect an end of turbulent blood flow within the audio dataset, etc.). However, the Korotkoff sounds can otherwise be detected (e.g., to identify a time stamp, timing, etc. for evaluating the datasets).

However the target cardiovascular parameters can otherwise be determined.

Validating the unvalidated device S400 functions to determine a validation state of the unvalidated device (e.g., whether the unvalidated device is valid or invalid as a device for measuring the cardiovascular parameter). Validating the unvalidated device can mean that the unvalidated device: consistently produces a result or product meeting its predetermined specifications, conform with user needs and intended use(s), and/or can otherwise be defined. The unvalidated device is preferably validated (or invalidated) across a patient population (e.g., for patients with common patient characteristics), but can be validated (or invalidated) for a particular patient or group of patients, for any patient (e.g., regardless of patient class or characteristics), and/or otherwise be validated (or invalidated). The unvalidated device is preferably validated (or invalidated) automatically, but can be validated (or invalidated) manually and/or otherwise be validated (or invalidated).

The validation status can last for a threshold amount of time (e.g., 1 day, 1 week, 1 month, 30 days, 2 months, 60 days, 3 months, 4 months, 6 months, 12 months, etc.), indefinitely, until an invalidation criterion occurs (e.g., damage to the previously unvalidated device, threshold shock, change in temperature, humidity, etc.), and/or for any suitable time. The validation status can be device specific, device agnostic, patient specific, patient characteristic specific (e.g., validated for particular patient subpopulations), patient agnostic, and/or can otherwise be specific or agnostic.

The validity of the unvalidated device is preferably determined based on a comparison of the cardiovascular parameter determined from the validated dataset to the cardiovascular parameter determined from the unvalidated dataset (e.g., for each patient, for each measured dataset, etc.). However, the validity of the unvalidated device can additionally or alternatively be determined based on the auxiliary dataset, by comparing the datasets in a different basis (e.g., such as a pressure wave or other format than as the cardiovascular parameter), and/or any suitable information. The comparison can include a threshold test, a statistical hypothesis test (e.g., Bayesian hypothesis testing, Akaike information criterion, etc.), a statistical analysis, a model (e.g., a statistical model), using pair analysis (e.g., a mixed model repeated analysis, paired analysis between validated and associated unvalidated datasets, paired analysis between validated and associated unvalidated cardiovascular parameters, etc.), and/or any suitable test. Examples of thresholds include: root mean square thresholds, mean error thresholds, a standard deviation threshold, width of a percentile (e.g., $50^{th}$, $75^{th}$, $80^{th}$, $90^{th}$, $95^{th}$, $99^{th}$, $99.5^{th}$, $99.9^{th}$, etc.) limit of agreement, covariance thresholds (e.g., as shown for example in FIGS. 6 and 7), variance thresholds, and/or any suitable threshold.

The comparisons can be per target cardiovascular parameter (e.g., separated for systolic and diastolic blood pressure, as shown for example in FIG. 8A, etc.), across a group of (e.g., a subset of, all, etc.) target cardiovascular parameters (e.g., aggregated test metric for systolic and diastolic blood pressure, as shown for example in FIG. 8B, etc.), and/or can otherwise be performed. In some variants, different threshold can be used for different target cardiovascular parameter comparisons. For example, a first threshold can be used for systolic blood pressure and a second threshold can be used for diastolic blood pressure. The first threshold can be larger than, smaller than, and/or equal to the second threshold. For instance, a threshold width of an associated 95$^{th}$ percentile limit of agreement for systolic blood pressure can be ±12 mmHg and a threshold width of an associated 95$^{th}$ percentile limit of agreement for diastolic blood pressure can be ±8 mmHg. In another example, a least square mean difference threshold (e.g., ±0.1 mmHg, ±1 mmHg, +5 mmHg, +8 mmHg, ±10 mmHg, +12 mmHg, +15 mmHg, ±20 mmHg, values or ranges therebetween, etc.) can be used, where the standard deviation threshold can be the same or different for systolic and diastolic blood pressure.

When the test cardiovascular parameter dataset (e.g., the unvalidated cardiovascular parameter dataset, unvalidated dataset, test dataset, etc.) achieves the threshold (e.g., when the test dataset agrees with the reference dataset), the unvalidated cardiovascular parameter device (e.g., unvalidated cardiovascular parameter monitor) is preferably validated. However, the unvalidated cardiovascular parameter device (e.g., unvalidated cardiovascular parameter monitor) can be invalidated, conditionally validated (e.g., for specific patient groups, for specific patients, for specific time ranges, for measuring specific conditions, for measuring cardiovascular parameters in particular conditions, etc.), and/or can otherwise be validated, invalidated, or have any suitable validation state.

In an illustrative example, the blood pressure (e.g., the systolic and diastolic blood pressure) measured from the pressure dataset (e.g., of an auscultatory dataset) can be compared S420 to a blood pressure determined from a plethysmogram dataset (e.g., an unvalidated blood pressure dataset) at approximately the same time (e.g., at a time stamp associated with a target cardiovascular parameter as determined in S300). When the auscultatory blood pressure and plethysmogram blood pressure are with a threshold of each other (e.g., 0.1 mmHg, 0.5 mmHg, 1 mmHg, 5 mmHg, 10 mmHg, etc.; ±1%, ±5%, ±10%, ±20%, etc.; etc.) the plethysmogram device can be validated S450 (for at least that patient). When the auscultatory blood pressure and plethysmogram blood pressure are not within a threshold of each other, the plethysmogram can be invalidated S450 (at least for that patient). In a variation of this example, when a confidence or credibility (e.g., 50%, 75%, 90%, 95%, 99%, 99.5%, 99.9%, etc.) that the blood pressure determined using the auscultatory device and the plethysmometer are the same (e.g., to within a threshold), the plethysmometer can be validated. However, the validity of the unvalidated device can otherwise be determined for each patient dataset.

The validity of the unvalidated device is preferably determined by performing the comparison for a predetermined number of patients. However, the validity can be determined for a single patient and/or any number of patients. When the comparison indicates that the unvalidated device is valid for a threshold number (e.g., 1, 10, 100, 1000, 10000, >10000 patients) and/or percentage of (e.g., <50%, 50%, 75%, 80%, 90%, 95%, 99%, 99.9%, >99.9%, 100%, etc.) patients, then the unvalidated device can be validated. When the comparison indicates that the unvalidated device is invalid for a threshold number (e.g., 1, 10, 100, 1000, 10000, >10000 patients) and/or percentage of (e.g., <50%, 50%, 75%, 80%, 90%, 95%, 99%, 99.9%, >99.9%, 100%, etc.) patients, then the unvalidated device can be invalidated. However, the unvalidated device can otherwise be validated or invalidated for a patient population.

When the unvalidated device is not validated (for a patient or patient population), the method can include reprocessing the datasets (e.g., checking for and mitigating an effect of outliers; ensuring that the datasets were properly aligned; modifying or updating the conversion from datasets to cardiovascular parameter; repeating S100, S200, and/or S300; etc.), increasing the number of patients tested, retesting one or more patients, identifying an individual or population (e.g., patient characteristic(s)) that the unvalidated device is not validated for, and/or can otherwise operate.

5. Illustrative Examples

Figure 9:
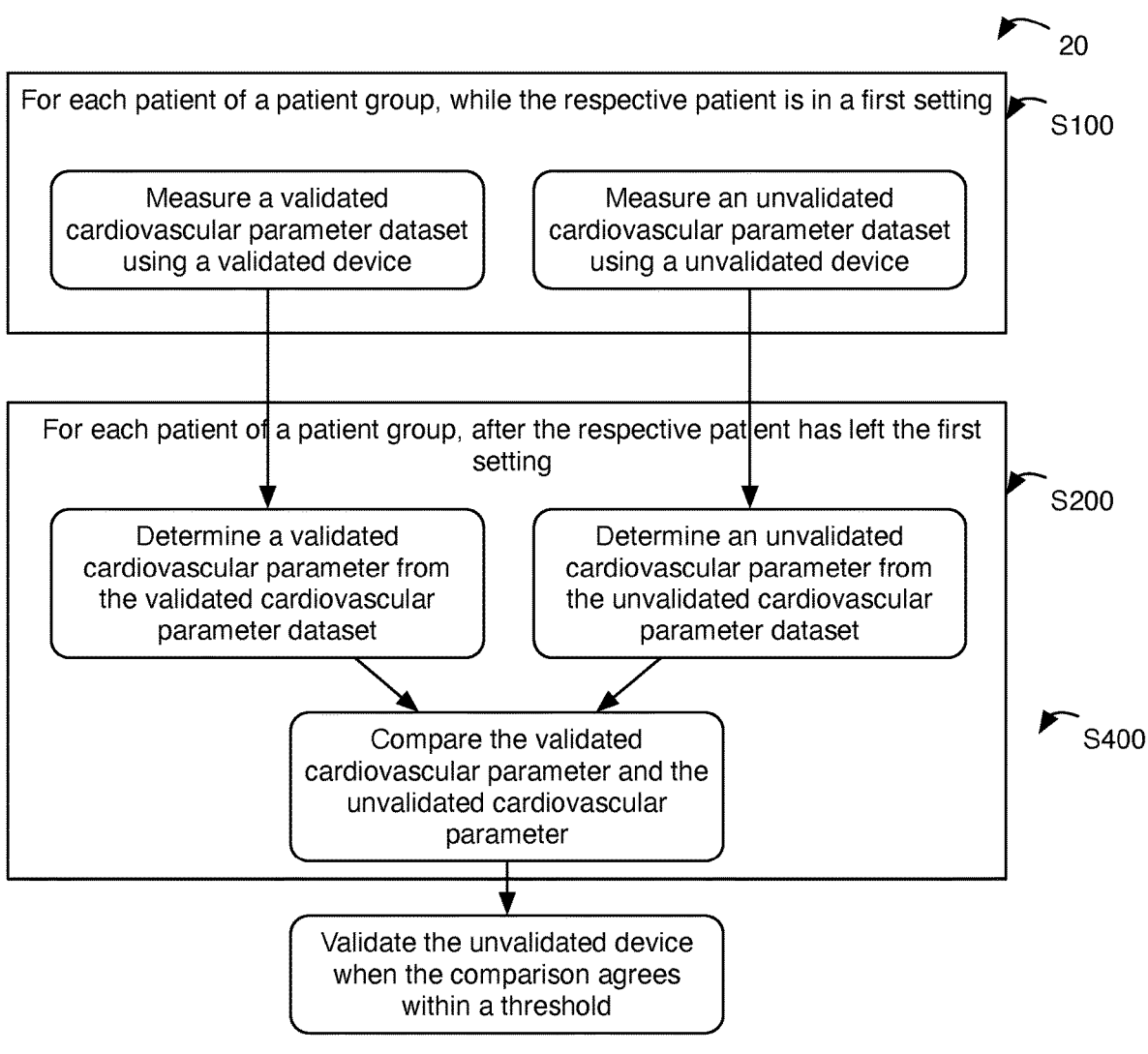
FIG. 9 is a flow chart representation of an example of the method.

In a first illustrative example (as shown for instance in FIG. 9), a method for determining a validation status for a blood pressure monitor can include: for a plurality of patients: at a first time, measuring a validated blood pressure for each patient of the plurality by: inflating and deflating a blood pressure cuff disposed on a first arm of the patient; contemporaneously with inflating and deflating the blood pressure cuff, measuring an audio signal at a frequency of at least 10 kHz using a digital stethoscope; and contemporaneously with inflating and deflating the blood pressure cuff, measuring a pressure dataset using a digital pressure gauge (e.g., manometer), wherein the pressure dataset includes an instantaneous pressure of the blood pressure cuff measured at a frequency of at least 10 Hz; contemporaneously with measuring the validated blood pressure, measuring an unvalidated blood pressure using the blood pressure monitor for each patient including: recording a time series of images of a finger region of the respective patient on a second arm of the respective patient; determining a pulse waveform from the time series of images; and extracting a set of fiducials from the pulse waveform, wherein the set of fiducials include fit parameters associated with a set of fitting functions used to fit the pulse waveform; and transforming the set of fiducials into the unvalidated blood pressure; at a second time, comparing the validated blood pressure to the unvalidated blood pressure; and determining the validation status of the blood pressure monitor based on the comparison. In this specific example, the validated blood pressure can include a systolic blood pressure approximately equal to a pressure of the pressure dataset measured when a first Korotkoff sound is detected in the audio signal and a diastolic blood pressure approximately equal to a pressure of the pressure dataset measured when a fourth or fifth Korotkoff sound is detected in the audio signal.

Figure 10:
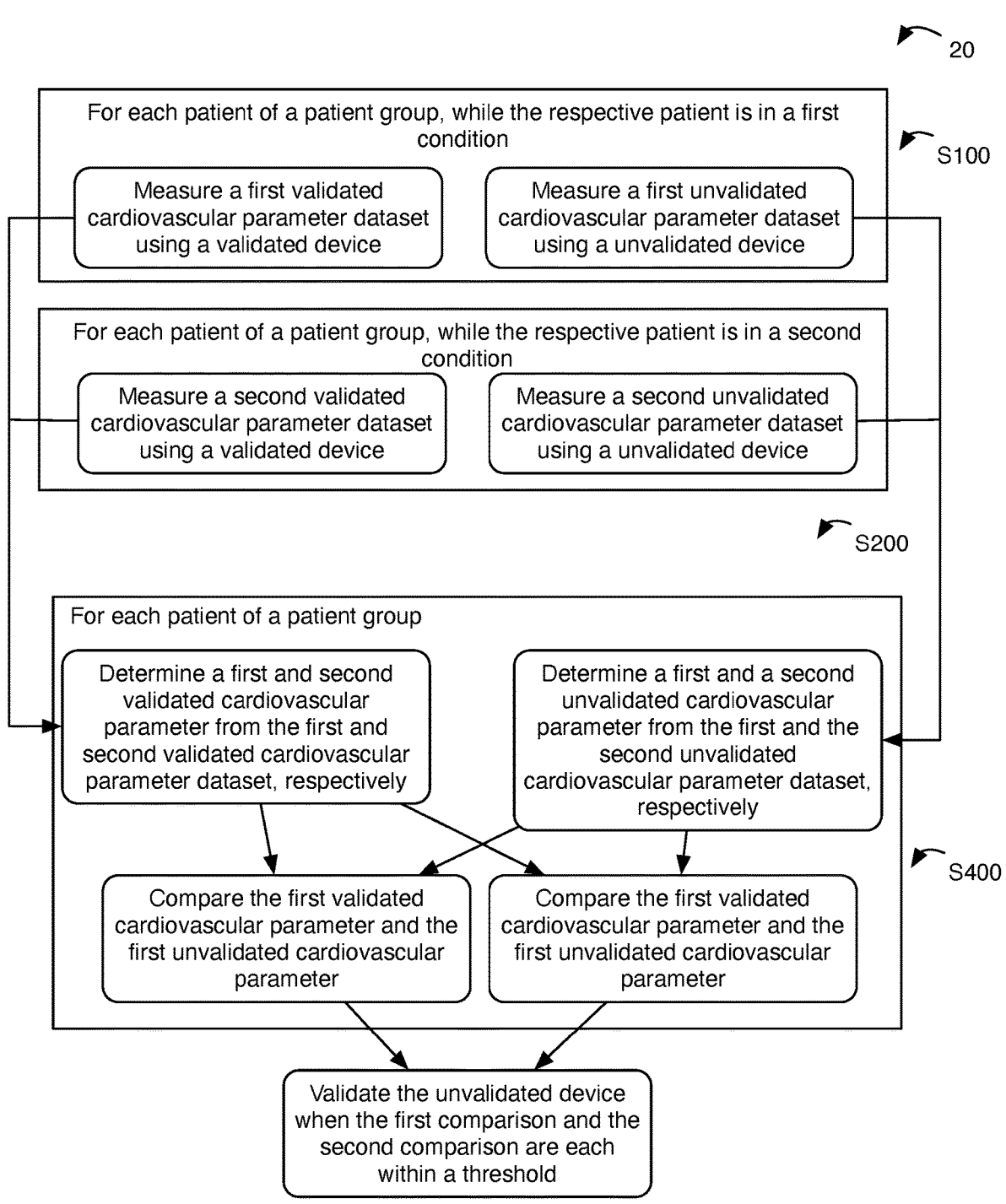
FIG. 10 is a flow chart representation of an example of the method.

In a variation of the first specific example (as shown for instance in FIG. 10), the method for determining a validation status for a blood pressure monitor can include repeating the measurements and analysis for the patients of the plurality of patients in a plurality of conditions. In these variations, the blood pressure monitor can be validated in a single condition, in all conditions, and/or in any suitable conditions. For instance, a paired analysis can be performed in each condition, and the unvalidated monitor can be validated in any or all conditions that meet a statistical threshold.

In a second variation of the first specific example (as shown for instance in FIG. 11), comparing the validated blood pressure to the unvalidated blood pressure can include averaging a plurality of unvalidated blood pressure values (e.g., blood pressure determined for waveforms within a threshold time of the validated blood pressure values, target blood pressure values, etc.). For instance, blood pressure values within ±5 seconds within ±3 pulse waves, etc. of the target blood pressure value time stamp can be averaged.

In a second specific example (that can be related to, combined with, include aspects of, etc. the first specific example), validating a cardiovascular parameter monitor comprising: receiving a plurality of reference cardiovascular parameter datasets, wherein each reference cardiovascular parameter dataset is associated with a patient of a plurality of patients, wherein each reference cardiovascular parameter dataset is converted to a reference cardiovascular measurement during post-hoc analysis; receiving a plurality of test cardiovascular parameter measurements, wherein each test cardiovascular parameter measurement includes a cardiovascular parameter measured for a patient of the plurality of patients using the cardiovascular parameter monitor, wherein each test cardiovascular parameter measurements is generated contemporaneously with a reference cardiovascular parameter dataset of the plurality of reference cardiovascular parameter dataset; validating the cardiovascular parameter monitor when a mean error or a standard deviation (or other statistical test) from a paired analysis of the plurality of reference cardiovascular measurements and the plurality of test cardiovascular parameter measurement is less than a statistical threshold.

The methods of the preferred embodiment and variations thereof can be embodied and/or implemented at least in part as a machine configured to receive a computer-readable medium storing computer-readable instructions. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

I claim:

1. A method for determining a validation status for a blood pressure monitor comprising:

for a plurality of patients:

(a) at a first time, measuring a validated blood pressure for each patient of the plurality by:

(i) inflating and deflating a blood pressure cuff disposed on a first arm of the patient;

(ii) contemporaneously with inflating and deflating the blood pressure cuff, measuring an audio signal at a frequency of at least 10 kHz using a digital stethoscope; and (iii) contemporaneously with inflating and deflating the blood pressure cuff, measuring a pressure dataset using a digital pressure gauge, wherein the pressure dataset comprises an instantaneous pressure of the blood pressure cuff measured at a frequency of at least 10 Hz;

(b) contemporaneously with measuring the validated blood pressure, (b) measuring an unvalidated blood pressure using the blood pressure monitor for each patient comprising:

(i) recording a time series of images of a finger region of the respective patient on a second arm of the respective patient;

(ii) determining a pulse waveform from the time series of images; and (iii) extracting a set of fiducials from the pulse waveform, wherein the set of fiducials comprise fit parameters associated with a set of fitting functions used to fit the pulse waveform; and (iv) transforming the set of fiducials into the unvalidated blood pressure;

(c) at a second time, comparing the validated blood pressure to the unvalidated blood pressure; and (d) determining the validation status of the blood pressure monitor based on the comparison;

wherein the validated blood pressure comprises a systolic blood pressure approximately equal to a pressure of the pressure dataset measured when a first Korotkoff sound is detected in the audio signal and a diastolic blood pressure approximately equal to a pressure of the pressure dataset measured when a fourth or fifth Korotkoff sound is detected in the audio signal.

2. The method of claim 1, wherein the first time and the second time differ by at least one hour.

3. The method of claim 1, wherein the systolic blood pressure and the diastolic blood pressure are determined in a post-hoc analysis of the audio signal and the pressure dataset, via a computing system.

4. The method of claim 1, wherein comparing the validated blood pressure to the unvalidated blood pressure comprises performing a mixed model repeated analysis, via computing system, wherein the validation status is positive when a mean error of the unvalidated blood pressure is about ±5 mmHg or a standard deviation of at most about 8 mmHg.

5. The method of claim 1, further comprising, for each patient of the plurality of patients, contemporaneously with inflating and deflating the blood pressure cuff, measuring an ECG dataset.

6. A method for determining a validation status for a photoplethysmography-based blood pressure monitor comprising:

(a) at a first time, measuring a validated blood pressure for a patient by:

(i) inflating and deflating a blood pressure cuff disposed on a first arm of the patient, (ii) contemporaneously with inflating and deflating the blood pressure cuff, measuring an audio signal at a frequency of at least 10 kHz using a digital stethoscope, and (iii) contemporaneously with inflating and deflating the blood pressure cuff, measuring a pressure dataset using a digital pressure gauge, wherein the pressure dataset comprises an instantaneous pressure of the blood pressure cuff measured at a frequency of at least 10 Hz;

(b) contemporaneously with measuring the validated blood pressure, measuring an unvalidated blood pressure using a photoplethysmography-based blood pressure monitor for the patient comprising:
(i) recording a time series of images of a finger region of a second arm of the patient,
(ii) determining a pulse waveform from the time series of images,
(iii) extracting a set of fiducials from the pulse waveform, wherein the set of fiducials comprise fit parameters associated with a set of fitting functions used to fit the pulse waveform, and
(iv) transforming the set of fiducials into the unvalidated blood pressure;
(c) at a second time, comparing the validated blood pressure to the unvalidated blood pressure;
(d) determining the validation status of the photoplethysmography-based blood pressure monitor based on the comparison; and
(e) outputting the validation status, wherein the validation status enables or disables the photoplethysmography-based blood pressure monitor for clinical use,
wherein the validated blood pressure comprises a systolic blood pressure approximately equal to a pressure of the pressure dataset measured when a first Korotkoff sound is detected in the audio signal and a diastolic blood pressure approximately equal to a pressure of the pressure dataset measured when a fourth or fifth Korotkoff sound is detected in the audio signal.

7. A method for determining a validation status for a blood pressure monitor comprising:
(a) at a first time, measuring a validated blood pressure for a patient by:
(i) inflating and deflating a blood pressure cuff disposed on a first arm of the patient,
(ii) contemporaneously with inflating and deflating the blood pressure cuff, measuring an audio signal at a frequency of at least 10 kHz using a digital stethoscope, and

(iii) contemporaneously with inflating and deflating the blood pressure cuff, measuring a pressure dataset using a digital pressure gauge, wherein the pressure dataset comprises an instantaneous pressure of the blood pressure cuff measured at a frequency of at least 10 Hz;
(b) contemporaneously with measuring the validated blood pressure, measuring an unvalidated blood pressure using the blood pressure monitor for the patient comprising:
(i) recording a time series of images of a finger region of a second arm of the patient,
(ii) determining a pulse waveform from the time series of images,
(iii) extracting a set of fiducials from the pulse waveform, wherein the set of fiducials comprise fit parameters associated with a set of fitting functions used to fit the pulse waveform, and
(iv) transforming the set of fiducials into the unvalidated blood pressure;
(c) using a computing system, automatically processing the validated blood pressure and the unvalidated blood pressure by comparing the validated blood pressure to the unvalidated blood pressure; and
(d) using the computing system, automatically determining the validation status of the blood pressure monitor based on the comparison,
wherein the validated blood pressure comprises a systolic blood pressure approximately equal to a pressure of the pressure dataset measured when a first Korotkoff sound is detected in the audio signal and a diastolic blood pressure approximately equal to a pressure of the pressure dataset measured when a fourth or fifth Korotkoff sound is detected in the audio signal.

* * * * *